US006210881B1

(12) United States Patent
Little et al.

(10) Patent No.: US 6,210,881 B1
(45) Date of Patent: *Apr. 3, 2001

(54) METHOD FOR REDUCING INHIBITORS OF NUCLEIC ACID HYBRIDIZATION

(75) Inventors: Michael C. Little, Baltimore; Oscar J. Llorin, Catonsville, both of MD (US); Matthew P. Collis, Seven Valleys, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/010,219

(22) Filed: Jan. 21, 1998

Related U.S. Application Data

(63) Continuation-in-part of application No. 08/774,476, filed on Dec. 30, 1996, now Pat. No. 5,763,185.

(51) Int. Cl.[7] .............. C12Q 1/68; C12N 13/00; C12N 1/06; A01N 47/140

(52) U.S. Cl. ............ 435/6; 435/173.9; 435/259; 514/514

(58) Field of Search .............. 435/6, 259, 173.9; 514/514

(56) References Cited

U.S. PATENT DOCUMENTS

| | | | |
|---|---|---|---|
| 4,483,920 | 11/1984 | Gillespie et al. | 435/6 |
| 5,010,183 | 4/1991 | Macfarlane | 536/27 |
| 5,393,672 | 2/1995 | Van Ness et al. | 436/94 |
| 5,482,834 | 1/1996 | Gillespie | 435/6 |
| 5,554,503 | 9/1996 | Down et al. | 435/6 |
| 5,571,894 | * 11/1996 | Wels et al. | 530/387.3 |
| 6,037,449 | * 3/2000 | Zhou et al. | 530/350 |

FOREIGN PATENT DOCUMENTS

| | | | |
|---|---|---|---|
| 0 389 063 | 3/1990 | (EP) | C07H/1/08 |
| 0 626 456 A1 | 5/1994 | (EP) | C12Q/1/68 |
| 0 745 849 A2 | 3/1996 | (EP) | G01N/35/50 |
| 0 770 689 A2 | 9/1996 | (EP) | C12Q/1/68 |
| WO 87/06621 | 11/1987 | (WO) | C12Q/1/68 |
| WO 92/08807 | 5/1992 | (WO) | C12Q/1/68 |
| WO 93/03167 | 2/1993 | (WO) | C12P/19/34 |
| PCT/US94/08638 | 2/1995 | (WO) | C12N/15/10 |

OTHER PUBLICATIONS

Maniatis et al. Molecular cloning a laboratory manual, p. 1.34–1.39, 1989.*

Goergen, B. et al. "A new, easy and safe method for the purification of nucleic acids for reliable PCR" *Experientia*; 50:790–791 (1994).

Higuchi, R. "Simple and Rapid Preparation of Samples for PCR" *Preparation of Samples for PCR*; 31–38 (1989).

Khan, G., et al., Inhibitory effects of urine on the polymerase chain reaction for cytomegalovirus DNA; *J. Clin. Pathol.*; 44, pp 360–365 (1991).

Buffone, G.J.; Improved Amplification of Cytomegalovirus DNA from Urine Purification of DNA with Glass Beads; *Clin. Chem.*, 37, pp 1945–1949 (1991).

(List continued on next page.)

*Primary Examiner*—W. Gary Jones
*Assistant Examiner*—J. Tung
(74) *Attorney, Agent, or Firm*—David W. Highet

(57) ABSTRACT

The present invention relates to a method for reducing the amount of substances inhibitory to nucleic acid hybridization in samples. The method is practiced prior to release of target nucleic acid from cells of interest and involves contacting the sample with an agent which solubilizes the inhibitory substances and does not effectuate release of nucleic acids from cells in the sample, and then the cells from the agent.

20 Claims, 4 Drawing Sheets

OTHER PUBLICATIONS

Erlich, Henry A., Ed., Principles and Applications for DNA Amplification: *PCR Technology*, Stockton Press, pp 33–34 (1989).

Ochert, A.S. et al., Inhibitory Effect of Salivary Fluids on PCR: Potency and Removal; *PCR Methods and Applications* 3, pp 365–368 (1994).

Frickhofen and Young, A rapid method of sample preparation for detection of DNA viruses in human serum by polymerase chain reaction; *J. Virol. Methods*, 35, pp 65–72 (1991).

Zeldis, Jerome B. et al., Direct Method for Detecting Small Quantities of Hepatitis B. Virus DNA in Serum and Plasma Using the Polymerase Chain Reaction; *J. Clin. Invest*, 84, pp 1503–1508 (1989).

Grimprel, E. et al., Use of Polymerase Chain Reaction and Rabbitt Infectivity Testing to Detect *Treponema pallidum* in Amniotic Fluid, Fetal and Neonatal Sera, and Cerebrospinal Fluid, *J. Clin. Microbiol.* 29, pp1711–1718 (1991).

Jiang, X. et al., Detection of Norwalk Virus in Stool by Polymerase Chain Reaction, *J. Clin. Microbiol* 30, pp 2529–2534 (1992).

Wilde, J. et al., Removal of Inhibitory Substances from Human Fecal Specimens for Detection of Group A Rotaviruses by Reverse Transcriptase and Polymerase Chain Reactions, *J. Clin. Microbiol.*, 28, pp 1300–1307 (1990).

Hubbard, M.J., Validation and rapid extraction of nucleic acids from alcohol–preserved ticks; *Experimental & Applied Acarology*, 19, pp 473–478 (1995).

Reek, Frans H. et al., Use of Multiscreen Plates for the Preparation of Bacterial DNA Suitable for PCR; *Biotechniques* (1995).

Sonthayanon, Piengchan et al.; Molecular Cloning, Sequencing and Amplification of Plasmodium vivaax–specific DNA for Use in Diagnosis by PCR; *Asia Pacific J. of M. Biol. and Biotech.*, 4, pp 118–122 (1996).

Shah, Jyotsna S. et al., Detection of *Mycobacterium tuberculosis* Directly from Spiked Human Sputum by Q–Beta Replicase–Amplified Assay; *J. of Clin. Microbio.*, 33, pp 322–328 (1995).

Delacourt, Christophe et al.; Use of polymerase chain reaction for improved diagnosis of tuberculosis in children; *J. Pediatrics*; 126, pp 703–709 (1995).

Lee, Jee Yeon et al., Rapid and Direct Detection of Vibrio vulnificus in Small Octopus (*Octopus variabilis*) Using Polymerase Chain Reaction; *J. Microbiol. and Biotech.*, 5, pp 181–187 (1995).

Cano, Raul J. et al.; Polymerase Chain Reaction Assay Coupled with Fluorescence Detection on Microwall Plates for *Listeria monocytogenes* in Foods; *J. of Food Protection*; 58, pp 614–620 (1995).

Bartolome, J. et al.; Detection of hepatitis C virus RNA in serum and peripheral blood mononuclear cells; *J. Hepatol.*, 17, pp S90–S93 (1993).

Rajagopalan, M.; A rapid protocol for isolation of RNA from mycobacteria; *Lett. Appl. Microbiol.*, 21, pp 14–17 (1995).

Chungue, Eliane et al., Ultra–Rapid, Simple, Sensitive, and Economical Silica Method for Extraction of Dengue Viral RNA from ClinicalSpecimens and Mosquitoes by Reverse Transcriptase–Polymerase Chain Reaction; *J. Med. Virol.*, 40, pp 142–154 (1993).

Shieh, Y.–S.C.; Methods to remove inhibitors in sewage and other fecal wastes for enterovirus detection by the polymerase chain reaction; *J. Virol. Methods*, 54, pp 51–66 (1995).

* cited by examiner

METHOD FOR REDUCING INHIBITORS OF NUCLEIC ACID HYBRIDIZATION

This application is a continuation in part of Ser. No. 08/774,476, filed Dec. 30, 1996 now U.S. Pat. No. 5,763,185.

BACKGROUND OF THE INVENTION

The field of the present invention broadly relates to nucleic acid hybridization. More specifically, the present invention relates to the reduction of substances in samples which inhibit nucleic acid hybridization events. Such events include nucleic acid probe hybridization to determine the presence and/or amount of a target nucleic acid, and nucleic acid primer hybridization for the initiation of a nucleic acid amplification process.

Nucleic acid amplification processes such as strand displacement amplification (SDA), polymerase chain reaction (PCR), ligase chain reaction (LCR), nucleic acid sequence based amplification (NASBA), transcription mediated amplification (TMA) and others are used to create multiple copies of a particular nucleic acid sequence(s) of interest (target sequence) which is present in lesser copy number in a sample. However, a number of substances commonly found in such samples cause inhibition of nucleic acid amplification processes, because of inhibition of the hybridization of primers to initiate the amplification process. Similarly, such substances inhibit direct nucleic acid probe hybridization reactions used for the detection of unamplified target nucleic acids.

An example of such nucleic acid hybridization inhibitory substances are porphyrin compounds derived from heme and hematin which are both commonly found in blood samples and inhibit PCR. (*PCR Technology*, Stockton Press, Henry A. Erlich, Ed. pp 33–34, 1989). Protocols using osmotic lysis and pelleting of nucleic and cell debris have been used to reduce the amount of these inhibitors.

Salivary samples have also been reported to contain PCR inhibitory substances. Ochert et al., *PCR Methods and Applications* 3, 365–368 (1994). Although the inhibitory substances were not identified, it was found that extended microwaving or boiling of the salivary sample totally removed PCR inhibition.

Frickhofen and Young, *J. Virol. Methods* 35, 65–72 (1991), report that heating of serum samples for 45 seconds at 70° C. improves PCR amplification of viral nucleic acid sequences. This improvement is theorized to be due to heat inactivation of serum enzymes such as aprotinin, leupeptin PMSF and pepstatin which are believed to be inhibitory to PCR processes.

Another approach for removing PCR inhibitory substances from serum prior to amplification of a viral nucleic acid sequence is taught by Zeldis et al., *J. Clin. Invest.* 84, 1503–1508 (1989). This approach involves adsorbing the virus to antibody coated microparticles, washing the microparticles, and then destroying the remaining proteins which may be inhibitory to PCR with proteinase K.

In attempting to detect *Treponema pallidum* in amniotic fluid, fetal and neonatal sera and cerebrospinal fluid by PCR, four different processes were attempted to remove PCR inhibitory compounds. Grimprel et al, *J. Clin. Microbiol.* 29, 1711–1718 (1991). Briefly, the four processes for removal of PCR inhibitory compounds were: (1) a boiling method wherein sample in a tube was placed in a boiling water bath for 10 minutes, cooled on ice, and then centrifuged; (2) a low-spin separation method wherein sample was added to sterile phosphate buffered saline and subjected to a series of centrifugations, then the pellet was resuspended and boiled for 10 minutes, after which it was cooled on ice; (3) an alkaline lysis extraction method wherein sample was boiled for 1.5 minutes in 1 M NaCl, 1 N NaOH and 0.1% SDS, then neutralized with 0.5 M Tris-HCl (pH 8.0), and then subjected to a series of extractions with phenol and chloroform-isoamyl alcohol, and precipitated with isopropyl alcohol; and (4) a spin extraction method wherein sample was subjected to low-spin separation as described in (2) above, followed by 10 minutes of boiling and one phenol-chloroform extraction before precipitation in cold absolute ethanol. The authors reported varying success of these methods dependent on the type of samples used.

With stool samples, polyethylene glycol precipitation was found to remove a significant amount of small particles and soluble substances which could be inhibitory to a reverse transcriptase-PCR process. Jiang et al, *J. Clin. Microbiol.* 30, 2529–2534 (1992). Following the precipitation, an extraction process was performed using the cationic detergent, cetyltrimethylammonium bromide (CTAB) in a high salt concentration in conjunction with phenol-chloroform extraction.

A different approach to removal of PCR inhibitory substances from stool samples is reported by Wilde et al., *J. Clin. Microbiol.* 28, 1300–1307 (1990). Before using PCR to detect rotavirus nucleic acid from stool samples, the extraction process was modified with an added step that utilized chromatographic cellulose fiber powder (CF11 powder) to purify the rotavirus RNA during a series of rapid washing and elution steps.

When performing a study to detect cytomegalovirus (CMV) in urine using PCR, it was found that urea is inhibitory to PCR. Khan et al., *J. Clin. Pathol.* 44, 360–365 (1991). This reference reports that the PCR inhibitory effects of urea in urine are effectively removed by simple dialysis or ultracentriftigation.

Another process to remove PCR inhibitory substances from urine before detection of CMV nucleic acid is reported by Buffone et al., *Clin. Chem.* 37, 1945–1949 (1991). This process occurs subsequent to release of the nucleic acid from the CMV organisms and uses fine glass beads to adsorb nucleic acid such that protein and other substances can be selectively eluted before recovery of the nucleic acid for amplification.

As evidenced by the references described above, most of the publication regarding nucleic acid amplification inhibition has related to PCR. However, these same substances which are inhibitory to PCR, as well as a number of other substances commonly found in clinical samples such as proteinaceous substances, EDTA, human DNA and iron have been found to be inhibitory to SDA, and other nucleic acid amplification processes as well.

Also, most of these methods to reduce or remove nucleic acid hybridization inhibiting substances involve rather time-consuming complicated steps which must be added to the sample processing methodology. Another problem with methods which utilize relatively severe processing steps or conditions, and/or require separation of target nucleic acid from other substances is the loss of some target nucleic acid sequence. Despite the ability of nucleic acid amplification processes to make multiple copies of target sequence (amplicons) from very few original targets, amplification efficiency and detection ability are improved if there are greater numbers of original targets in the sample. The greater detection ability can be very important when processing particularly difficult to detect samples such as acid fast Bacillus (AFB) smear negative *Mycobacterium tuberculosis* samples.

SUMMARY OF THE INVENTION

In order to address the problems associated with the presence of substances inhibitory to nucleic acid hybridization in samples and thus, achieve the benefits of more efficient amplification and improved detection of target nucleic acid sequences, the present invention provides a method for reducing the amount of such substances in samples by, prior to lysis of cells in the sample which contain nucleic acid to be amplified, contacting the sample with an agent which does not effectuate the release of nucleic acid from the cells, and then separating the cells from the agent.

Examples of some useful agents for use in the present invention include chaotropes such as guanidine thiocyanate, sodium perchlorate and sodium thiocyanate. Also, the separation of cells from the agent is generally accomplished by a wash and centrifugation step with a solution in which the agent is soluble.

BRIEF DESCRIPTION OF THE DRAWINGS

The various objects, advantages and novel features of the invention will be more readily appreciated from the following detailed description when read in conjunction with the appended figures, in which.

DETAILED DESCRIPTION OF THE INVENTION

Figure 1:
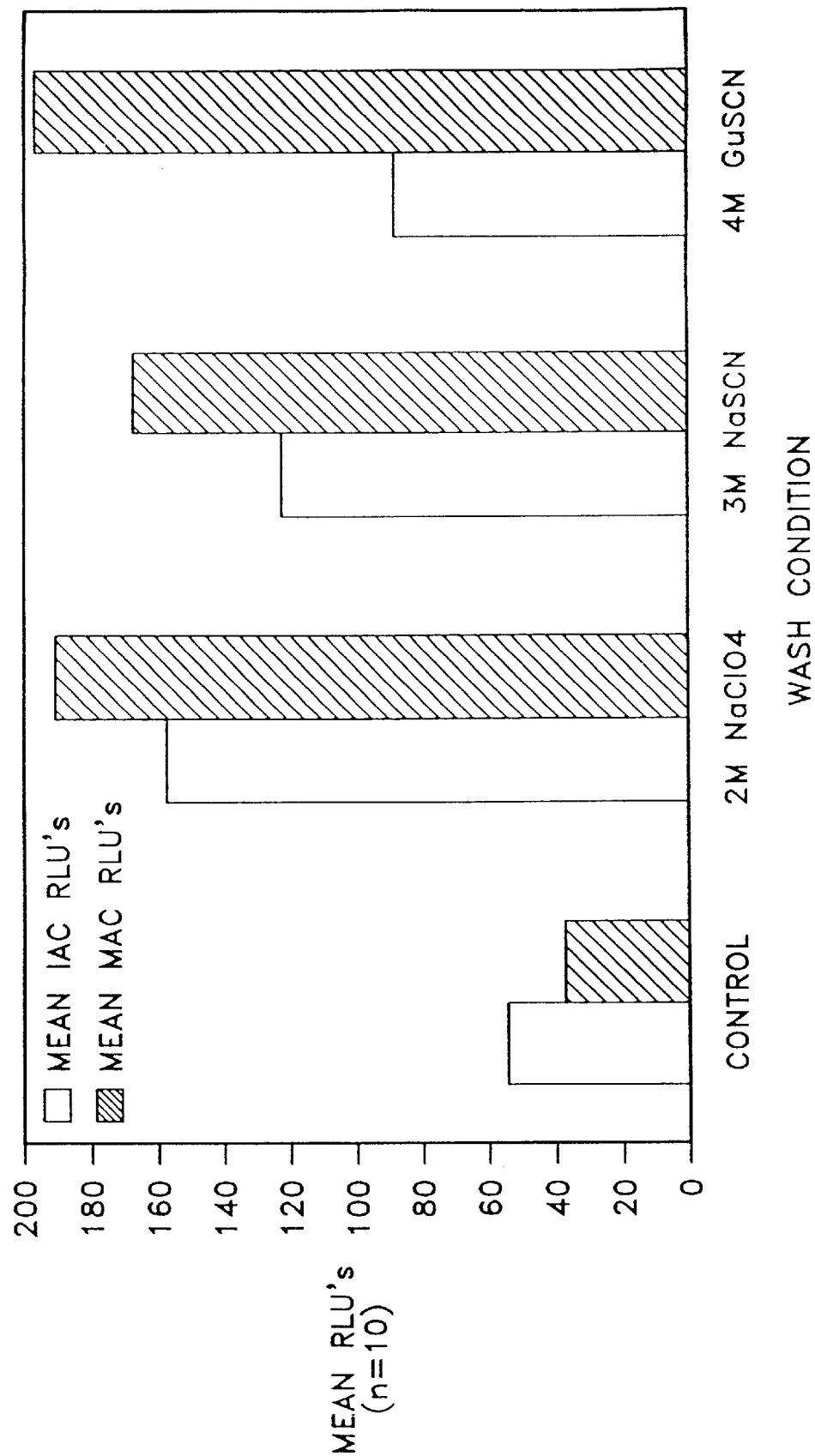
FIG. 1 is a graphical representation of the results of an experiment conducted to determine whether the method of the present invention reduces the amount of nucleic acid amplification inhibition from a clinical sample as compared to a control standard sample processing method.

As stated above, the present invention relates to a method for reducing the amount of substances which are inhibitory to nucleic acid hybridization processes from samples containing cells with nucleic acid which will be subjected to a hybridization process. In the method, an agent which solubilizes such substances and does not effectuate the release of nucleic acid from cells is contacted with a sample prior to lysis of cells in the sample such that cells containing nucleic acid will remain in the sample. Then, such cells are separated from the agent.

The results of this method were particularly unexpected because of the complexity of some of the processes tried by others to remove inhibitory substances as evidenced by the descriptions in the Background section above. Also, the agents used in the method of the present invention were generally believed by those skilled in the art to be useful for effectuating the release of nucleic acid from cells by cell wall lysis or solubilization, as evidenced by various references such as U.S. Pat. No. 5,482,834 wherein chaotropic salts are taught to be useful specifically for the solubilization or lysis of cells. Generally, such agents were used in combination with heat to lyse or solubilize cells.

The cell wall lysogenic properties of chaotropes such as guanidinium thiocyanate (GuSCN) have also been reported in references such as Hubbard et al., *Experimental & Applied Acarology* 19, 473–478 (1995), Boom et al., *J. Clin. Microbiol.* 28 495–503 (1990), Reek et al., *BioTechniques* 19, 282–285 (1995), Chungue et al. *J. Med. Virol.* 40, 142–145 (1993) and Shah et al., *J. Clin. Microbiol.* 33, 322–328 (1995). Similarly, chaotropes and detergents such as GuSCN have been extensively utilized in the extraction of nucleic acid from cells as taught in references such as Delacourt et al., *J. Pediatrics* 126, 703–710 (1995), Lee and Choi, *J. Microbiol. & Biotechnol.* 5, 181–187 (1995), Cano et al., *J. Food Protection* 58, 614–620 (1995), Bartolome et al., *J. Hepatol.* 17, s90–s93 (1993), Rajagopaian et al., Lett. Applied Microbiol. 21, 14–17 (1995) and Shieh et al, *J. Virol. Methods* 54, 51–66 (1995). Thus, the quick and simple method of the present invention wherein cells in a sample are contacted (washed) with such an agent prior to cell lysis to remove nucleic acid hybridization inhibitory substances was unexpected in view of other processes being used in the art.

Also, one of the advantages of the method of the present invention is the ability to increase the initial yield of target nucleic acid from the cells in a sample. Although nucleic acid amplification processes are capable of creating many copies of a target sequence (amplicons) from very few initial targets, it is beneficial to start the amplification process with as many initial targets as possible. Other processes for removing nucleic acid hybridization inhibitory substances subsequent to lysis of the cells are notoriously inefficient, because they are based on separation of nucleic acid from other substances in the lysate, and thus, many initial targets are not recovered. In the present method, where the inhibitory substances are removed prior to cell lysis, such subsequent separation is not necessary, and better yields of initial target are achieved.

The samples which may be subjected to the method of the present invention include virtually all human and veterinary clinical samples such as sputum samples, blood samples, urine samples, cerebrospinal fluid ("CSF") samples and others, environmental samples such as water, air and soil samples, and food samples. The samples which may be subjected to the method of the present invention are suspected of containing cells with a target nucleic acid sequence to be subjected to a hybridization process such as direct probe hybridization or primer hybridization for initiation of an amplification process.

The types of cells present in the samples subjected to the method of the present invention include the cells of virtually all organisms. The method of the present invention is particularly useful with samples suspected of containing cells of infectious organisms. As shown in the Examples below, the method of the present invention was effective with the cells of infectious organisms such as *Mycobacterium tuberculosis, Bacillus stearothermophilus*, Group B streptococcus, Group A streptococcus, *E. coli, Candida albicans, Staphylococcus epidermidis, Neiserria gonorrhoeae, Chlamydia trachomatis* and *Enterococcus faecalis*. Because the primary criterium for determining which types of cells can be effectively treated using the method of the present invention is whether the cells are lysed by contact with the agent, a routine screening assay can be used by one of ordinary skill in the art with a reasonable expectation of success to identify such types of cells.

More specifically, a sample containing the cells of interest is exposed to the agent of the method. Subsequently, the cells of the sample are washed to remove any nucleic acid which may be present from cells lysed by the agent. Then, the cells are resuspended and lysed by application of heat and agitation with particles (beads). Finally, a dye specific for nucleic acid is added to the sample, and the amount of dyed nucleic acid from the treated sample is compared to a control which was subjected to the same conditions except for contact with the agent.

If the amount of nucleic acid from the treated sample is substantially equivalent to the amount of nucleic acid from the control, then samples of those cells can be effectively treated using the method of the present invention. That is, contact with the agent of the present invention did not effectuate lysis of the cells.

Substances which are inhibitory to nucleic acid hybridization processes and typically found in such samples include proteinaceous materials and human DNA in human samples and animal DNA in veterinary samples. As discussed in the Background section above, these substances are known to be inhibitory of nucleic acid amplification processes such as SDA, PCR, LCR, NASBA, TMA and others.

The first step of the method of the present invention is to contact the sample with an agent in which the inhibitory substance is soluble and which will not effectuate the release of nucleic acid from cells. This contacting may occur at any time prior to the lysis of cells to release target nucleic acid. However, a preferred time for contacting the cells such an agent is after some manipulation of the sample to concentrate the location of the cells or pellet the cells. Typically, such concentration is a result of centrifugation, but may also result from filtration or selective adsorption.

Such concentration of the cells provides a greater assurance that the agent will contact the cells, and permits more efficient use of the agent due to a defined location of cells. The contacting of cells with the agent is preferably a relatively brief wash of the cells. Typically, the contacting of cells and agent is for up to about five minutes.

Many agents are useful in the method of the present invention. Examples of such useful agents include chaotropes and detergents which are well known to those skilled in the art such as Triton X-100, Triton X-114, NP-40, Brij 35, Brij 58, Tween 20, Tween 80 nonionic detergents, octyl glucoside, octyl thioglucoside, Chaps a zwitterionic detergent, sodium iodide, sodium perchlorate, potassium iodide, sodium thiocyanate, potassium thiocyanate, guanidine thiocyanate, guanidine isothiocyanate, sodium trichloroacetate, sodium trifluoroacetate and urea. Other agents useful in the method of the present invention can be identified by one of ordinary skill in the art with a reasonable expectation of success by performing routine screening assays directed towards the two primary characteristics of such agents; degree of solubilization of nucleic acid hybridization inhibitory substances and lack of effectuation of release of nucleic acid from cells.

Briefly, an agent is contacted with cells, the cells centrifuged, and amplification reaction for a target nucleic acid sequence common to the cells performed on the supernatant in a routine screening assay. If the target sequence is amplified, then the agent does not meet the requirements for use in the method of the present invention, because it has effectuated the release of nucleic acid from the cells, whereas lack of amplification of the target sequence and amplification of an internal control sequence would indicate that the agent may be useful in the method of the present invention. Then, the agent which has not effectuated the release of nucleic acid from the cells is brought into contact with known nucleic acid hybridization inhibitory substances, and the degree of solubilization of the inhibitory substance quickly determined in a routine screening assay. Those agents which solubilize the inhibitory substance are useful in the method of the present invention.

The concentration and amount of the agent used in the method of the present invention is dependent on the type of sample being subjected to the method. Examples of suitable concentrations of chaotropes and detergents for use in the method of the present invention are presented below in Table 1.

TABLE 1

Chaotrope/Detergent Concentrations

| Chaotrope/Detergent | Concentrations |
| --- | --- |
| Triton X-100 | 0.024 mM, 0.24 mM, 2.4 mM |
| Triton X-114 | 0.021 mM, 0.21 mM, 2.1 mM |
| NP-40 | 0.029 mM, 0.29 mM, 2.9 mM |
| Brij 35 | 0.009 mM, 0.09 mM, 0.9 mM |
| Brij 58 | 0.0077 mM, 0.077 mM, 0.77 mM |
| Tween 20 | 0.006 mM, 0.06 mM, 0.6 mM |
| Tween 80 | 0.0012 mM, 0.012 mM, 0.12 mM |
| Octyl glucoside | 2.4 mM, 24 mM |
| Octyl thioglucoside | 0.9 mM, 9.0 mM |
| Chaps | 0.9 mM, 9.0 mM |
| NaI | 2M, 3M, 4M, 5M, 6M |
| NaClO$_4$ | 2M, 3M, 4M, 5M, 6M |
| KI | 2M, 3M, 4M, 5M, 6M |
| NaSCN | 2M, 3M, 4M, 5M, 6M |
| KSCN | 2M, 3M, 4M, 5M, 6M |
| Guanidine Isothiocynate | 2M, 3M, 4M, 5M, 6M |
| Sodium trichloroacetate | 2M, 3M, 4M, 5M, 6M |
| Sodium trifluoroacetate | 2M, 3M, 4M, 5M, 6M |
| Urea | 2M, 3M, 4M, 5M, 6M |

Generally, the volume of the agent used in the method of the present invention is at least equal to the volume of sample. More particularly, the volume:volume ratio of the agent to the sample is from about 1:1 to about 5:1. Also, generally, it is preferable that the agent be prepared as a basic solution, with most preferable pHs for particular agents being determined by a routine screening assay based, for example, on the experiments presented in Example 3 hereof, in which a 6.0 M guanidine isothiiocyanate solution at pH 9.0 was found to be particularly beneficial for reducing the amount of nucleic acid hybridization inhibitory substances. The optimal concentration (molarity) of a particular agent may also be determined using the same type of routine screening assay based on the experiments presented in Example 3 hereof Also, generally, the agent is brought into contact with the sample at room temperature.

When the agent is brought into contact with cells of the sample, nucleic acid hybridization inhibitory substances are solubilized by the agent, thus washing such substances from the walls of the cells. Because suitable agents do not effectuate release of nucleic acid from the cells, loss of target nucleic acid when the agent is separated from the cells is not a concern.

However, the agents used in the method of the present invention may also adversely effect nucleic acid hybridization processes, and thus, such agents are subsequently separated from the cells. Such separation may be accomplished by any suitable means such as filtration or wash and centrifugation with or without a buffer in which the agent is soluble. Preferably, such a buffer is used in order to assure removal of the inhibitory substances as well as the agent prior to cell lysis. Thus, when such cells are lysed, the target nucleic acid is presented in an environment with minimal amounts of substances which are inhibitory to the hybridization process to which the target nucleic acid will be subjected.

A variety of processes are currently used to prepare target nucleic acids in samples for hybridization or amplification. For example, sputum samples which are processed to amplify mycobacterial nucleic acid sequences are typically subjected to a NALC/NaOH process. The method of the present invention may be particularly useful with mycobacterial samples subjected to such a NALC/NaOH process due to its selective solubilization of NALC/NaOH pellets to reduce clumping of such samples. Similarly, other types of clinical samples are subjected to other well known standard processes, for example, centrifugation for large volume samples such as blood and urine. The method of the present invention may be used before, as part of, or after those standard processes, provided that the method is practiced prior to lysis of cells containing the target nucleic acid.

The method of the present invention does not require the quantitative binding and releasing of target nucleic acid from a binding surface, and thus permits the use of more sample than is conventionally utilized in nucleic acid based hybridization or amplification assays. This ability to use more sample confers greater sensitivity to such assays, as there is more target nucleic acid present at the initial stages of the assay. The selectivity of the agents in solubilizing inhibitory substances, but not concomitantly solubilizing target nucleic acid or cell walls is one of the characteristics of the agents which contributes to the results of the method of the present invention as evidenced by the Examples set forth below.

The following examples illustrate specific embodiments of the invention described herein. As would be apparent to skilled artisans, various changes and modifications are possible and are contemplated within the scope of the invention described.

EXAMPLE 1

Comparison of Method of the Present Invention to Control Samule Processing Method The purpose of this Example was to determine if a method of the present invention reduces the amount of nucleic acid amplification inhibition from a clinical sample and therefore yields better target detection values compared to a control standard sample processing method.

MATERIALS
SAMPLE PROCESSING REAGENTS:
  Sodium Perchlorate (Sigma)
  Sodium Thiocyanate (Sigma)
  Guanidine Thiocyanate (Sigma)
  Reverse Osmosis DIstilled ("RODI") $H_2O$
  MycoPrep (BBL)
  MAC/TB Sample Diluent
  Phosphate buffer solution (BBL)
  Zirconium Bead Containing Capsules (Becton Dickinson)
  Clinical sputum samples; Sample ID 785, 657, 634, 8594, 8894, 13883, 8396, 13867, 13088, 146
  M. avium complex ("MAC") mycobacterial cells AMPLIFICATION REAGENTS
  RODI $H_2O$
  500 mM $KPO_4$
  50X PBA
  50X dCAG
  5 mg/ml BSA
  100 mM DTT
  50% Trehalose
  1 U/ul UDG
  192 mM Magnesium
  50X dU
  5 U/ul UDI
  Bst 120 U/ul
  Bso BI 160 U/ul
  Internal Amplification Control ("IAC") $10^3$
  55% Glycerol
  DMSO
  Human Placental DNA
  Anti-Foam
  Target Diluent
DETECTION REAGENTS
  M. tb. Hybridization nix
  MAC Probes
  Hybridization Diluent
  IAC hybridization mix
  System Fluid
  Wash Fluid
  Assay Device ("AD")
  LUMIPHOS 530
  2.0 ml Labcraft® tubes
  MAC Assay Calibrators
  Assay Calibrators
PROCEDURE:
  $NaClO_4$ was prepared at 2M in distilled water. NaSCN was prepared at 3M in distilled water. GuSCN was prepared at 4M in distilled water. Each of these three chaotrope solutions was dispensed into ten 2.0 ml LabCraft® tubes at 1.0 ml/tube. A 1.0 ml aliquot of MAC/TB sample buffer was dispensed into ten 2.0 ml LabCraft® tubes.

Ten clinical sputum samples were thawed to room temperature. MycoPrep buffer was added at an equal volume to the sputum sample volumes, and the samples were vortexed and maintained at room temperature for 15 minutes.

Phosphate buffer was then added to each sample to adjust the total volume of each sample to 50 ml. The samples were vortexed and centrifuged at 3,000 relative centrifugal force (RCF) for 20 minutes. The supernate was decanted and 2.0 ml of Phosphate buffer was added to each sample and the samples were vortexed. MAC cells at 75 particles/ml were spiked into the resulting sample.

A 500 ul aliquot of each sample was then dispensed into all four wash buffer types described (sample buffer, 2M $NaClO_4$, 3M NaSCN and 4M GuSCN at 1.0 ml from above). The samples were vortexed and centrifiged at 12,200 RCF for 3.0 minutes. The supernate was decanted and the pellet resuspended with 1.0 ml of MAC/TB sample buffer, and then centrifuged at 12,200 RCF for 3.0 minutes. Again, the supernate was decanted, the pellet resuspended with 1.0 ml of MAC/TB sample buffer, and centrifuged at 12,200 RCF for 3.0 minutes.

A zirconium beads containing capsule was inserted into each tube, and each pellet resuspended with 400 ul of MAC/TB sample buffer. The samples were heated for 30 minutes at 105° C. in a forced hot air oven to lyse mycobacterial cells, and render any mycobacterial organisms non-infectious. The samples tubes were then loaded into a Savant CellPrep® instrument which was run on a setting of 5.0 m/s for 45 seconds to separate nucleic acids from other cellular components. The samples were then farther processed in a MAC/TB amplification and detection system as follows.

Thermophilic SDA was performed essentially as described in published European Patent Application No. 0 684 315 in a reaction mixture comprising 25 mM potassium phosphate pH 7.6, 100 µg/mL acetylated bovine serum albumin (BSA), 0.5 mM dUTP, 0.2 mM each dATP and dGTP, and 1.4 mM 2' deoxycytidine 5'—O—(I-thiotriphosphate) (α-thio dCTP), 12% glycerol, 6.5 mM magnesium acetate, 0.5 µM amplification primers, 0.05 µM bumper primers, 50 ng human placental DNA, 12.5 units Bst polymerase, 160 units BsoBI, 1 units uracil-N-glycosylase (UNG) and 2 units uracil-N-glycosylase inhibitor (Ugi).

Prior to addition of the enzymes and initiation of the amplification reaction, the samples were boiled for 2 minutes. The samples were then incubated at 41° C. for 2 minutes. and the UNG was added to degrade any contaminating amplicons. After a 30 minute. incubation with UNG the samples were transferred to 52° C. for 5 minutes. The enzyme mix (Bst polymerase, BsoBI, Ugi and glycerol) was added and amplification was allowed to proceed for 30 minutes. at 52° C. The reaction was stopped by boiling for 5 minutes.

The amplification products were detected in a chemiluminescent assay essentially as described by C. A. Spargo, et al. (1993. *Molec. Cell. Probes* 7, 395–404). Alkaline phosphatase-labeled detector probes for M. tb., MAC and IAC, biotinylated capture probes for M. tb., MAC and IAC, and the samples were added to the well of a rnicrotiter plate coated with streptavidin and incubated for 50 minutes. at 37° C. The wells were then washed three times with stringency buffer. LUMIPHOS (Lumigen, Inc.) was added and the reaction was incubated for 30 minutes. at 37° C. Luminescence was detected in a luminometer (Dynatech) and relative light units (RLUs) were recorded.

RESULTS

The results are provided in the table below, as the mean M. tb., MAC and IAC values for the ten samples, and in graphical form in FIG. 1.

| CHAOTROPE | TB (RLU) | MAC (RLU) | IAC (RLU) |
|---|---|---|---|
| 2M NaClO$_4$ | 0.42 | 189.1 | 157.4 |
| 3M NaSCN | 0.42 | 166.6 | 122.5 |
| 4M GuSCN | 0.5, 11.91* | 196.1 | 87.7 |
| CONTROL | 0.6, 2.33* | 36.2 | 54.1 |

*Both wash methods had the same sample with positive M. tb. values, indicating a possible erroneous diagnosis at the clinical site.

CONCLUSIONS

The data of this Example indicates that, statistically, there is no difference in the IAC values for any of the wash conditions, however it is interesting that the mean values for all the agent conditions are higher than the control wash procedure. The data also show statistically the 4M GuSCN condition produced higher specific MAC RLU values than any of the other three conditions. This indicates that the method of the present invention as practiced herein does not damage the mycobacterium and in fact, in the case of 4M GuSCN, improves the recovery of the MAC organism and subsequently the target DNA.

EXAMPLE 2

Screening Clinical Samples for Inhibition of Nucleic Acid Amplification

The purpose of this Example was to screen clinical samples for inhibition of nucleic acid amplification.

MATERIALS
SAMPLE PROCESSING REAGENTS
  MycoPrep Reagent
  BBL Phosphate buffer, pH 6.8
  TB/MAC Sample Diluent
  Smear negative, culture negative sputum from N. Carolina Public Health, Sample ID 8207, 1514, 13472, 14199, 13847, 3675,6401, 4691, 13545, 13711, 9939, 12227, 12228, 12161, 8406, 782, 13547, 13448, 13506, 13319, 13420, 243, 103
  Zirconium Bead Containing Capsules
AMPLIFICATION REAGENTS
  Same as for Example 1, and a IN2 Plasmid Control
ASSAY REAGENTS
  Same as for Example 1.
PROCEDURE:

Twenty-three clinical sputum samples were thawed to room temperature. Any sputum with greater than 12 ml of sputum was split into a separate tube, such that the range of volumes for any one processed sputum sample was 7.5–12 ml.

MycoPrep reagent was added to the sputa samples at an equal volume to the sputum volume. The samples were vortexed and maintained at room temperature for 15 minutes. The volume of each sputum solution was adjusted to 50 ml with Phosphate buffer.

The solutions were centrifuged at 3,000 RCF for 20 minutes. The supernate was decanted from each sample pellet and 2.0 ml of Phosphate buffer was added to each tube. The samples were aliquoted into 500 ul aliquots in 2.0 ml LabCraft® tubes. One sample of each type was maintained at room temperature and the remaining samples were stored at −70° C.

One ml of MAC/TB sample buffer was added to each sample maintained at room temperature. The samples were centrifuged at 12,200 RCF for 3.0 minutes. The supernate was decanted, 1.0 ml of MAC/TB sample buffer was added to each tube and the tubes were centrifuged at 12,200 RCF for 3.0 minutes. The supernate was decanted, a zirconium bead containing capsule was added to each tube and 400 ul of MAC/TB sample buffer was dispensed into each tube. The tubes were heated in a forced hot air oven at 105° C. for 30 minutes to lyse mycobacterial cells, and render any mycobacterial organisms non-infectious. The tubes were agitated on a Savant CellPrep™ instrument using setting 5.0 m/s for 45 seconds. Thermophilic Strand Displacement (tSDA) using the liquid MAC/TB triplex assay and detection procedures as described in Example 1 were used to generate the results from this experiment in Relative Light Units (RLUs).

RESULTS:

The results are presented in the table below.

| SAMPLE ID | M TB (RLU) | MAC (RLU) | IAC (RLU) |
|---|---|---|---|
| 8207 | 0.3 | 5.3 | 0.3 |
| 13506 | 0.3 | 3.8 | 0.7 |

| SAMPLE ID | M TB (RLU) | MAC (RLU) | IAC (RLU) |
|---|---|---|---|
| 13472 | 0.3 | 3.9 | 12 |
| 14199 | 0.3 | 2.1 | 44 |
| 13847 | 0.3 | 2.9 | 116 |
| 3675 | 0.3 | 2.4 | 24 |
| 6401 | 0.4 | 0.9 | 0.7 |
| 4691 | 0.4 | 1.3 | 2 |
| 13545 | 0.4 | 4.0 | 16 |
| 13711 | 0.3 | 2.3 | 69 |
| 9939 | 0.3 | 2.0 | 10 |
| 1514 | 0.3 | 2.7 | 50 |
| 12228 | 0.3 | 0.7 | 7 |
| 12161 | 0.2 | 3.5 | 6 |
| 8406 | 0.4 | 1.6 | 8 |
| 782 | 0.3 | 1.5 | 0.4 |
| 13547 | 0.6 | 2.4 | 41 |
| 13319 | 0.9 | 3.0 | 10 |
| 243 | 0.5 | 0.7 | 106 |
| 13448 | 0.4 | 1.1 | 0.8 |
| 13420 | 0.4 | 1.2 | 54 |
| 103 | 0.8 | 0.5 | 123 |
| 12227 | 0.5 | 1.4 | 66 |

CONCLUSION

Of the twenty-three clinical samples assayed in the MAC/TB system, nine produced IAC values of less than 10 RLUs, indicating severe inhibition of the amplification/detection reaction by the clinical sample. These inhibitory specimens produced under "standard" sample wash conditions were further processed as shown in the Examples below.

EXAMPLE 3 pH and Molarity Adjustments to Chaotrope Solution

The purpose of this Example was to determine if the pH and molarity of the GuSCN wash can be adjusted to remove more inhibitors from clinical samples.

MATERIALS

SAMPLE PROCESSING REAGENTS

Negative NALC pellet sample Nos. 6401, 8406, 782, 13448, 13506 from Example 2

Guanidine Isothiocyanate(GuSCN) Gibco BRL

MAC/TB sample buffer

Zirconium Bead Containing Capsules 500 mM Potassium Phosphate ($KPO_4$)

5N NaOH Ricca

M. tb. mycobacterial cells

AMPLIFICATION REAGENTS

Same as for Example 1.

ASSAY REAGENTS

Same as for Example 1.

PROCEDURE

A negative NALC inhibitory pool was prepared by dispensing 1.0 ml of sample 782, and 500 ul of samples 6401, 8406, 13448 and 13506 into a 2 ml polypropylene tube. M. tb. organisms were spiked into the inhibitory pool at 200 particles/ml (7.5 particles/final tSDA reaction). The GuSCN solutions prepared are summarized in the table below. The pH 7.0 and 9.0 solutions were adjusted to the indicated pH with 5N NaOH.

| CHAOTROPE SOLUTIONS | |
|---|---|
| 6.0M GuSCN, pH 4.9 | 4.0M GuSCN, pH 5.6 |
| 6.0M GuSCN, pH 7.0 | 4.0M GuSCN, pH 7.0 |
| 6.0M GuSCN, pH 9.0 | 4.0M GuSCN, pH 9.0 |

Each GuSCN solution was dispensed into one 2.0 ml LabCraft® tube at 1.0 ml/tube. The spiked negative NALC inhibitory pool was dispensed into each tube containing GuSCN at 500 ul/tube.

The tubes were vortexed briefly and the tubes were centrifuged at 12,200 RCF for 3.0 minutes. The supernate was decanted and 1.0 ml of MAC/TB sample buffer was dispensed into each tube and the tubes were centrifuged at 12,200 RCF for 3.0 minutes. The supernate was decanted and 1.0 ml of MAC/TB sample buffer was dispensed into each tube. The tubes were centrifuged at 12,200 RCF for 3.0 minutes. The supernate was decanted and a zirconium bead containing capsule was inserted into each tube.

MAC/TB sample buffer was decanted into each tube at 400 ul/tube. The tubes were heated in a forced hot air oven at 105° C. for 30 minutes. The tubes were agitated on a Savant CellPrep™ instrument using a setting 5.0 m/s for 45 seconds. tSDA using the liquid MAC/TB triplex assay and detection procedures described in Example 1 were used to generate the results from this experiment in Relative Light Units (RLUs).

Figure 2:
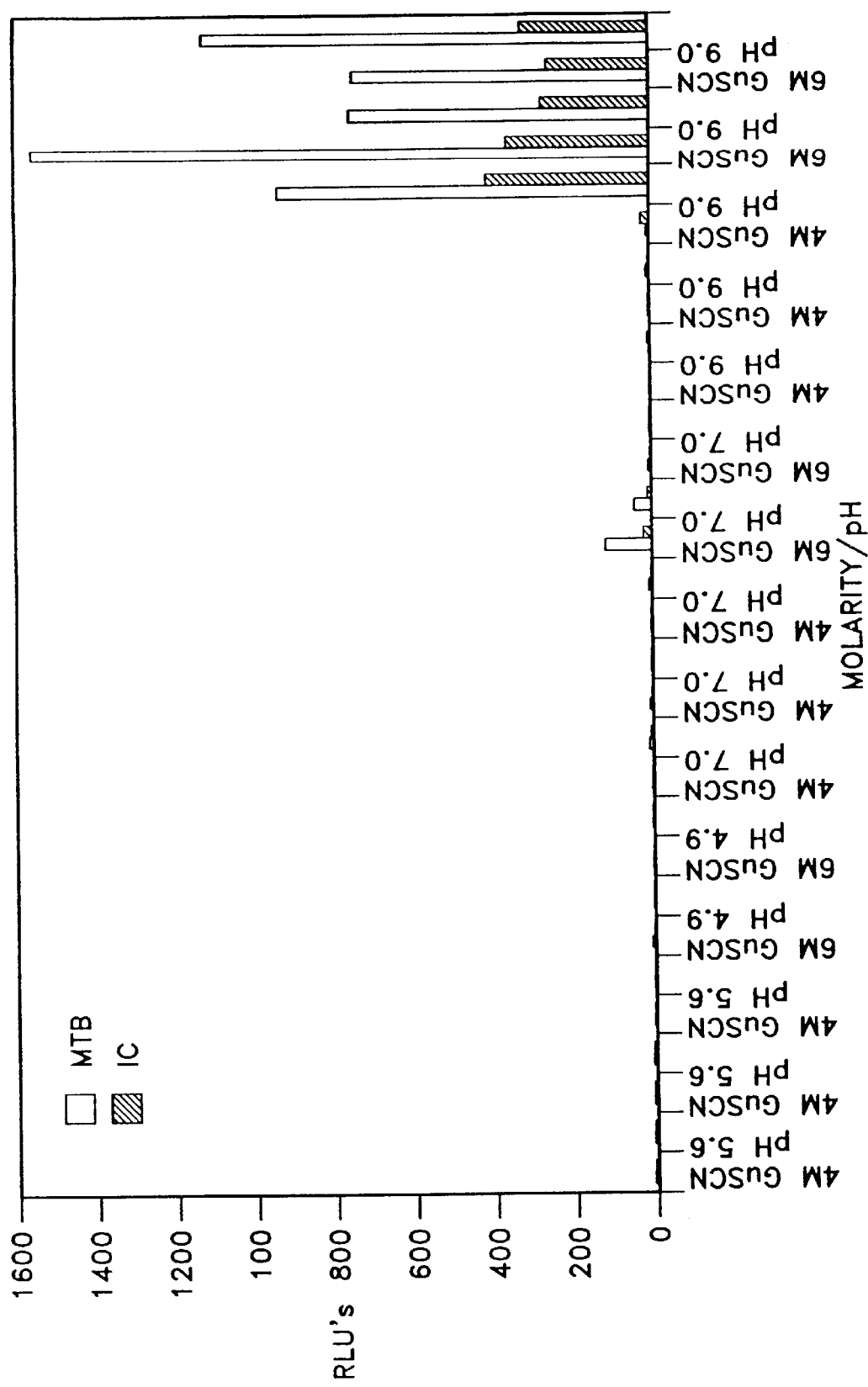
FIG. 2 is a graphical representation of the results of an experiment conducted to determine optimal pH and concentration values for a particular agent used in the method of the present invention.

RESULTS:

Results are presented in the table below, and in graphical form in FIG. 2.

| GuSCN(M) | pH | M TB RLUs | MAC RLUs | IAC RLUs |
|---|---|---|---|---|
| 4 | 5.7 | 2.4 | 0.3 | 1.9 |
| 6 | 4.9 | 1.5 | 0.4 | 0.7 |
| 4 | 7 | 2.4 | 0.4 | 1.3 |
| 6 | 7 | 32.8 | 0.4 | 6.6 |
| 4 | 9 | 2.6 | 0.4 | 5.3 |
| 6 | 9 | 1022.7 | 0.4 | 320.4 |

Note: The M. tb., MAC and IAC values are the means of five replicate amplification/detection samples.

CONCLUSION:

The 6.0 M, pH 9.0 GuSCN condition produced statistically better M. tb. and IAC RLU values than the other conditions, without producing non-specific MAC values. This indicates that a greater amount of nucleic acid hybridization inhibitors are removed using the 6.0 M, pH 9.0 GuSCN solution, without releasing target nucleic acid from Mycobacterium.

EXAMPLE 4

GuSCN(at 6 M and pH 9.0) Wash Using M. tb. Spiked Negative Clinical Samples

The purpose of this Example was to determine if clinical samples spiked with M. tb., and washed with the 6 M GuSCN pH 9.0 solution will remove unwanted nucleic acid hybridization inhibitors and allow amplification and detection of specific M. tb. DNA target.

MATERIALS

SAMPLE PROCESSING REAGENTS

Negative NALC pellet samples Nos. 8207, 1514, 13472, 14199, 13847, 3675, 6401, 4691, 13545, 13711, 9939, 12227, 12228, 12161, 8406, 782, 13547, 13448, 13506, 13319, 13420, 243, 103

Guanidine Isothiocyanate (GuSCN) Gibco BRL
MAC/TB sample buffer
Zirconium Bead Containing Capsules
500 mM Potassium Phosphate (KPO$_4$)
5 N NaOH Ricca AMPLIFICATION REAGENTS
Same as for Example 1.

ASSAY REAGENTS
Same as for Example 1.

PROCEDURE:

GuSCN solution was prepared at 6 M with 200 mM KPO$_4$ and was adjusted to pH 9.0 with 5 N NaOH as in Example 3. M. tb. organisms were spiked into 500 ul of each clinical sample from the Materials section of Example 2 at 200 particles/ml (7.5 particles/amplification reaction). Some of these samples from Example 2 were inhibitory to nucleic acid hybridization. M. tb. was spiked into 500 ul of MAC/TB buffer at 200 particles/ml and was labeled "sample processing control".

The GuSCN solution was dispensed into one 2.0 ml LabCraft® tube at 1.0 ml and the tube was labeled "GuSCN negative control". One ml of the 6 M, pH 9.0 GuSCN solution was dispensed into each clinical sample tube.

The tubes were vortexed and centrifuged at 12,200 RCF for 3.0 minutes. The supernate was decanted and 1.0 ml of MAC/TB buffer was dispensed into each tube and the tubes were centrifuged at 12,200 RCF for 3.0 minutes. The supernate was decanted and 1.0 ml of MAC/TB sample buffer was dispensed into each tube and the tubes were centrifuged at 12,200 RCF for 3.0 minutes. The supernate was decanted and a zirconium capsule was added to each tube. MAC/TB sample buffer was added to each tube at 400 ul/tube. The tubes were heated and agitated as described in the above Examples. tSDA using the liquid MAC/TB triplex assay and detection procedures described in Example 1 were used to generate the results from this experiment in Relative Light Units (RLUs).

RESULTS

Figure 3A:
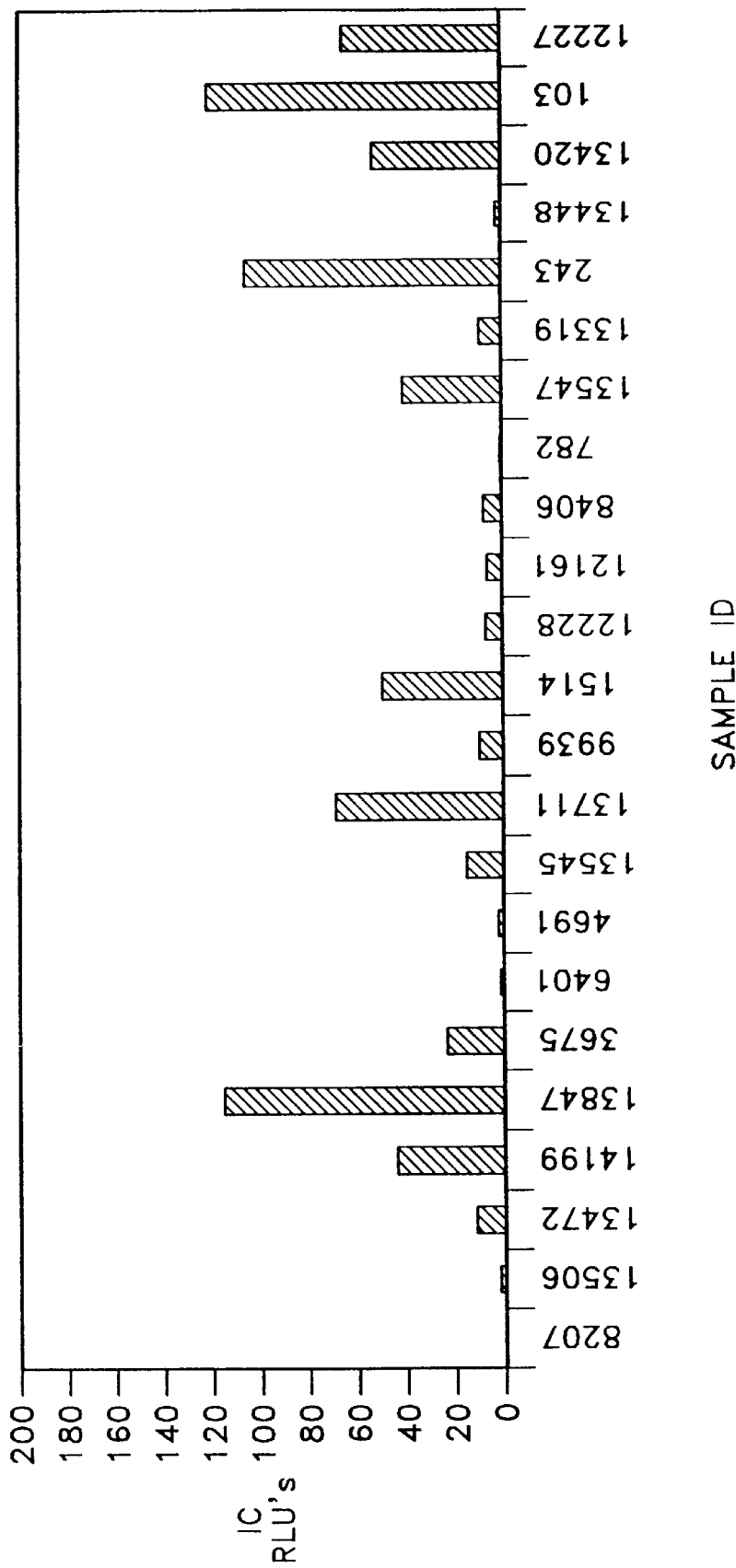
FIG. 3A is a graphical representation of the results of an experiment showing the effectiveness of the method of the present invention in reducing the amount of nucleic acid hybridization inhibitors from clinical samples.
Figure 3B:
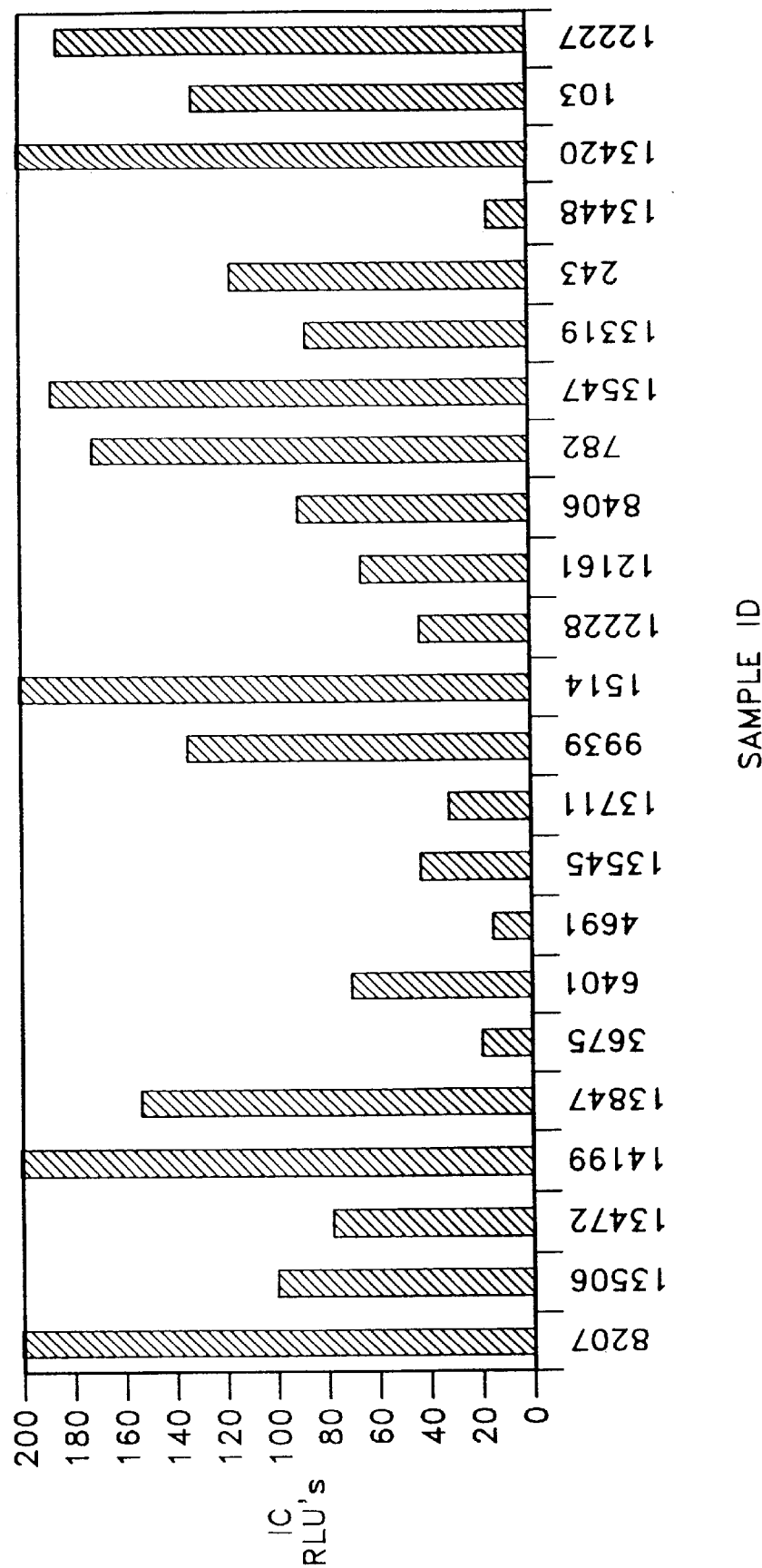
FIG. 3B is a graphical representation of the results of another experiment showing the effectiveness of the method of the present invention in reducing the amount of nucleic acid hybridization inhibitors from clinical samples.

The results are presented in a table below as the mean of three amplification replicates from each processed sample and in graphical form in FIG. 3.

| CLINICAL SAMPLE ID | M TB (RLUs) | IAC (RLUs) |
|---|---|---|
| 8207 | 1515.7 | 298.9 |
| 1514 | 1290.5 | 200.8 |
| 13472 | 223.5 | 79.6 |
| 14199 | 1004.8 | 263.4 |
| 13847 | 1342.1 | 154.3 |
| 3675 | 294.7 | 20.2 |
| 6401 | 279.5 | 71.6 |
| 13545 | 396.5 | 43.6 |
| 13711 | 275.5 | 32.8 |
| 9939 | 335 | 134.6 |
| 12227 | 1144.1 | 185.4 |
| 12228 | 297.7 | 43.6 |
| 12161 | 778.1 | 66.6 |
| 8406 | 478.6 | 90.9 |
| 4691 | 344.6 | 15.3 |
| 13547 | 1271.9 | 188 |
| 13448 | 358.5 | 16.3 |
| 13506 | 1470.4 | 101.8 |
| 13319 | 993.7 | 88 |
| 13420 | 1490.5 | 305 |
| 243 | 1406.2 | 117.9 |
| 103 | 1052.2 | 132.5 |
| 782 | 158.9 | 171.3 |
| GuSCN NEG. CTRL. | 1.8 | 91.7 |
| M. tb and buffer control | 568.5 | 37.9 |

CONCLUSION

Twenty-three IAC values gave acceptable tSDA values of greater than 10 RLUs, indicating that the amplification reaction was not inhibited. In addition, M tb. at 7.5 particles/amplification reaction was detected in every spiked sample as evidenced from specific to background RLU ratios of less than 88.2:1 for each sample. In Example 2, it was demonstrated that five of the clinical samples using no GuSCN wash had inhibitory IAC values of less than 10 RLUs. Improvements in nearly all samples (even those which were shown to be inhibitory by low signal generation in Example 2) were achieved with the method of the present invention as practiced in this Example.

EXAMPLE 5

Determination of Types of Cells Effectively Treated Using the Method of the Present Invention The purpose of this experiment was determine if treatment of a variety of different types of organisms with an agent useful in the method of the present invention would lyse the organism as evident by a loss of organism DNA prior to centrifugation.

SAMPLE ORGANISMS:

M. tuberculosis

Bacillus stearothermophilus

Group B streptococcus

Group A streptococcus

E. coli

Candida albicans

Staphylococcus epidermidis

N. gonnorhoeae

Chlamydia LGV II

Enterococcus faecalis

BUFFER REAGENTS

Phosphate buffer

PBS/BSA

Capsules containing zirconium beads

AGENTS

GuSCN NP-40

All organism samples except Chlamydia LGVII were grown and standardized to a McFarland 10 and each solution was transferred to three centrifuge tubes/solution at 1.0 ml/tube. Chlamydia LGV II at $1.4 \times 10^9$ Elementary bodies/ml was transferred to three centrifuge tube at 1.0 ml/tube. NP-40 detergent at 0.29 mM was dispensed into one tube of each solution type at 0.5 ml/tube. 6.0M GuSCN was dispensed into one tube of each solution type at 0.5 ml/tube. The final tube of each set for each organism was a control tube which was not exposed to an agent. All the tubes were centrifuged at 12,000 g for 3.0 minutes. The supernate was decanted from each tube and a zirconium bead containing capsule was added to each tube. The cell pellets were re-suspended with 1.0 ml of phosphate buffer. The tubes were placed in a lysolyzer for 30 minutes at 105° C. The tubes were then placed in a FastPrep™ cell disrupter for 45 seconds at a setting of 5.0 m/s.

Each solution from above was assayed for DNA content by preparing DNA standards in Tris EDTA buffer and diluting the experimental samples 1:100 in Tris EDTA buffer. Oligreen dye was added to standards and samples and the results were measured in a fluorometer using an excitation wavelength of 480 and an emission wavelength of 520.

The results are set forth in the table below.

| ORGANISM | TREATMENT | ng DNA./ML | % RECOVERY COMPARED TO CONTROL |
|---|---|---|---|
| B. stearothermophilus | GuSCN | 5840 | 31 |
| B. stearothermophilus | NP-40 | 18816 | 99 |
| B. stearothermophilus | Control | 18994 | — |
| Candida albicans | GuSCN | 86319 | 181 |
| Candida albicans | NP-40 | 93564 | 196 |
| Candida albicans | Control | 47717 | — |
| E. faecalis | GuSCN | 96043 | 147 |
| E. faecalis | NP-40 | 97408 | 149 |
| E. faecalis | Control | 65400 | — |
| Chlamydia LGV II | GuSCN | 29550 | 43 |
| Chlamydia LGV II | NP-40 | 56454 | 83 |
| Chlamydia LGV II | Control | 68362 | — |
| M. tuberculosis | GuSCN | 53251 | 102 |
| M. tuberculosis | NP-40 | 64224 | 123 |
| M. tuberculosis | Control | 52211 | — |
| E. coli | GuSCN | 148905 | 95 |
| E. coli | NP-40 | 190594 | 122 |
| F. coli | Control | 156150 | — |
| N. gonnorheae | GuSCN | 13801 | 5.4 |
| N. gonnorheae | NP-40 | 163606 | 63.7 |
| N. gonnorheae | Control | 256855 | — |
| Group B streptococcus | GuSCN | 89847 | 78 |
| Group B streptococcus | NP-40 | 116079 | 100 |
| Group B streptococcus | Control | 115932 | — |
| Group A streptococcus | GuSCN | 133237 | 70 |
| Group A streptococcus | NP-40 | 166085 | 88 |
| Group A streptococcus | Control | 115932 | — |
| S. epidermidis | GuSCN | 22067 | 64 |
| S. epidermidis | NP-40 | 29361 | 85 |
| S. epidermidis | Control | 34443 | — |

Although samples of B. stearothermophilus, Chiamydia LGV II and N. gonorrhoeae produced results that were lower when the organism was treated with GuSCN than with NP-40, NP-40 treatment of the organisms resulted in no dramatic loss in recovery of organism DNA for any sample. Thus, one of ordinary skill in the art would have a reasonable expectation of success in determining, without undue experimentation, which types of organisms are susceptible to the method of the present invention for reducing the amount of inhibitory substances from samples of various organisms. In general, the method used above is effective as a quick screening method to determine which organisms will lyse using treatments in accordance with the method of the present invention.

While the invention has been described with some specificity, modifications apparent to those with ordinary skill in the art may be made without departing from the scope of the invention. Various features of the invention are set forth in the following claims.

That which is claimed is:

1. A method for reducing the amount of substances which are inhibitory to nucleic acid hybridization processes from a sample containing cells comprising the steps of:
    (a) prior to lysis of the cells, contacting said cells with an agent which (i) solubilizes said substances, (ii) does not effectuate release of nucleic acid from said cells; and (iii) is a chaotrope or a detergent; and
    (b) separating said cells from said agent.

2. The method of claim 1 wherein the agent is selected from the group consisting of Triton X-100, Triton X-114, NP-40, Brij 35, Brij 58, Tween 20, Tween 80, octyl glucoside, octyl thioglucoside, Chaps, NaI, NaClO$_4$, KI, NaSCN, KSCN, guanidine isothiocynate, sodium trichloroacetate, sodium trifluoroacetate, and urea.

3. The method of claim 1 wherein said agent is a chaotrope.

4. The method of claim 3 wherein the chaotrope is guanidine isothiocyanate.

5. The method of claim 4 wherein guanidine isothiocyanate is present in a solution with a basic pH.

6. The method of claim 5 wherein the pH is about 9.0.

7. The method of claim 5 wherein the concentration of guanidine isothiocyanate is about 6 M.

8. The method of claim 1 wherein the separation is by wash and centrifugation.

9. The method of claim 1 wherein said agent is a detergent.

10. The method of claim 1 wherein prior to step (a), the cells are pelleted.

11. In a method of preparing a sample for a nucleic acid assay, the improvement comprising, prior to release of nucleic acid from cells in a said sample;
    (a) contacting the cells with an agent which (i) solubilizes substances which are inhibitory to nucleic acid hybridization, (ii) does not effectuate release of nucleic acid from said cells, and (iii) is a chaotrope or a detergent; and
    (b) separating said cells from said agent.

12. The method of claim 11 wherein the agent is selected from the group consisting of Triton X-100, Triton X-114, NP-40, Brij 35, Brij 58, Tween 20, Tween 80, octyl glucoside, octyl thioglucoside, Chaps, NaI, NaClO$_4$, KI, NaSCN, KSCN, guanidine isothiocynate, sodium trichloroacetate, sodium trifluoroacetate, and urea.

13. The method of claim 11 wherein said agent is a chaotrope.

14. The method of claim 13 wherein the chaotrope is guanidine isothiocyanate.

15. The method of claim 14 wherein guanidine isothiocyanate is present in a solution with a basic pH.

16. The method of claim 15 wherein the pH is about 9.0.

17. The method of claim 15 wherein the concentration of guanidine isothiocyanate is about 6 M.

18. The method of claim 11 wherein the separation is by wash and centrifugation.

19. The method of claim 11 wherein said agent is a detergent.

20. The method of claim 11 wherein prior to step (a), the cells are pelleted.

* * * * *